(12) United States Patent
Leigh

(10) Patent No.: US 8,733,494 B1
(45) Date of Patent: May 27, 2014

(54) COIL RETENTION SYSTEMS FOR IMPLANTABLE MEDICAL DEVICES

(71) Applicant: Charles Roger Aaron Leigh, North Epping (AU)

(72) Inventor: Charles Roger Aaron Leigh, North Epping (AU)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 13/782,029

(22) Filed: Mar. 1, 2013

(51) Int. Cl.
*H04R 29/00* (2006.01)
*H04R 9/00* (2006.01)

(52) U.S. Cl.
USPC .............................. 181/129; 607/136; 607/137

(58) Field of Classification Search
USPC .................. 607/137, 55, 56, 57, 136; 600/25; 623/10; 381/312; 181/129, 130
See application file for complete search history.

(56) References Cited

U.S. PATENT DOCUMENTS

| 6,178,353 | B1 | 1/2001 | Griffith et al. |
| 6,348,070 | B1 | 2/2002 | Teissl et al. |
| 6,838,963 | B2 | 1/2005 | Zimmerling et al. |
| 7,386,143 | B2 | 6/2008 | Easter et al. |
| 8,024,047 | B2 * | 9/2011 | Olson et al. ...................... 607/61 |
| 2005/0004629 | A1 | 1/2005 | Gibson et al. |
| 2008/0009920 | A1 * | 1/2008 | Gibson et al. .................... 607/57 |
| 2009/0299437 | A1 * | 12/2009 | Zimmerling .................... 607/57 |
| 2011/0022120 | A1 | 1/2011 | Ball et al. |
| 2012/0172659 | A1 | 7/2012 | Ball et al. |
| 2012/0238799 | A1 | 9/2012 | Ball et al. |

FOREIGN PATENT DOCUMENTS

WO    2011011409 A1    1/2011

* cited by examiner

*Primary Examiner* — Christopher D Koharski
*Assistant Examiner* — Michael Carey
(74) *Attorney, Agent, or Firm* — Edell, Shapiro & Finnan, LLC

(57) ABSTRACT

Presented herein are coil retention systems for use in implantable medical devices. In certain embodiments, a coil retention system comprises an implantable non-magnetized member having a central aperture and an external magnet also having a central aperture. The external magnet is configured to magnetically couple to the implantable non-magnetized member. In certain embodiments, the external magnet and the implantable non-magnetized member have corresponding annular shapes so as to self-align with one another.

20 Claims, 14 Drawing Sheets

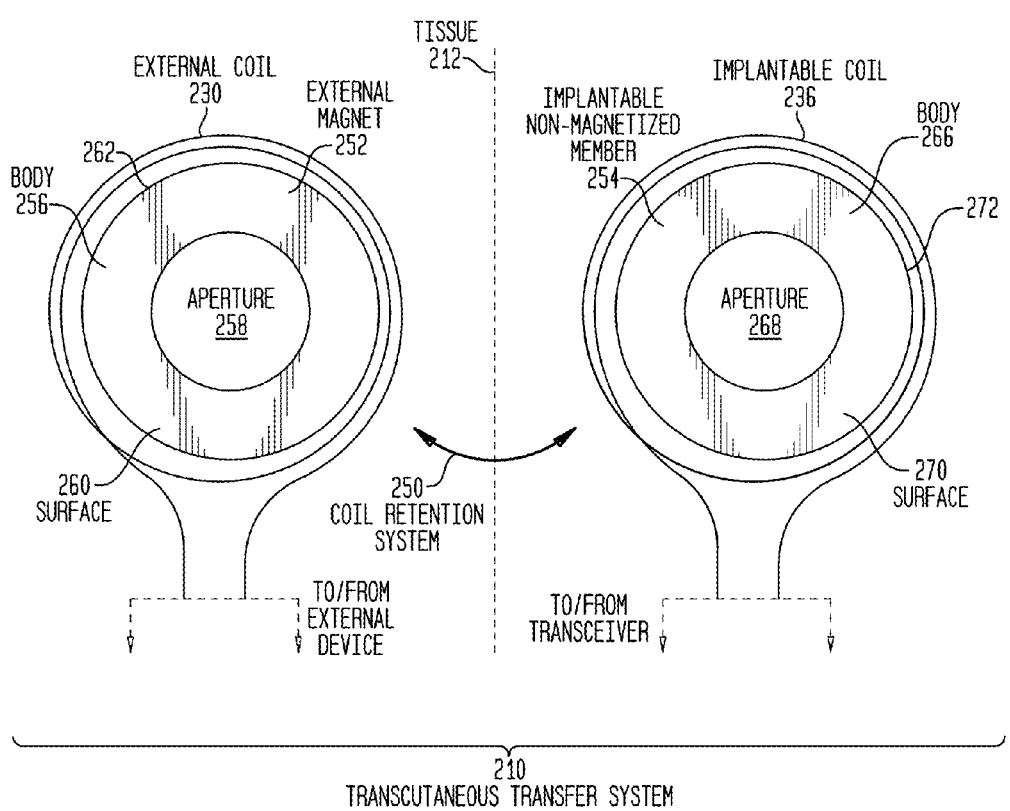

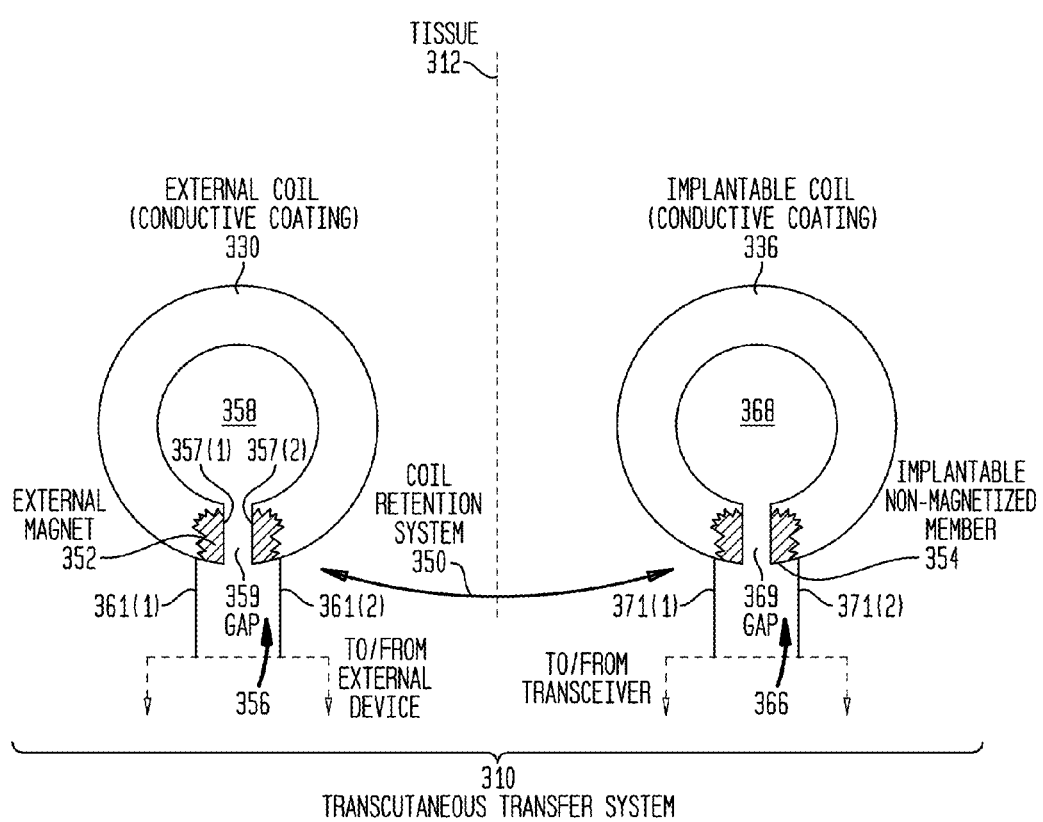

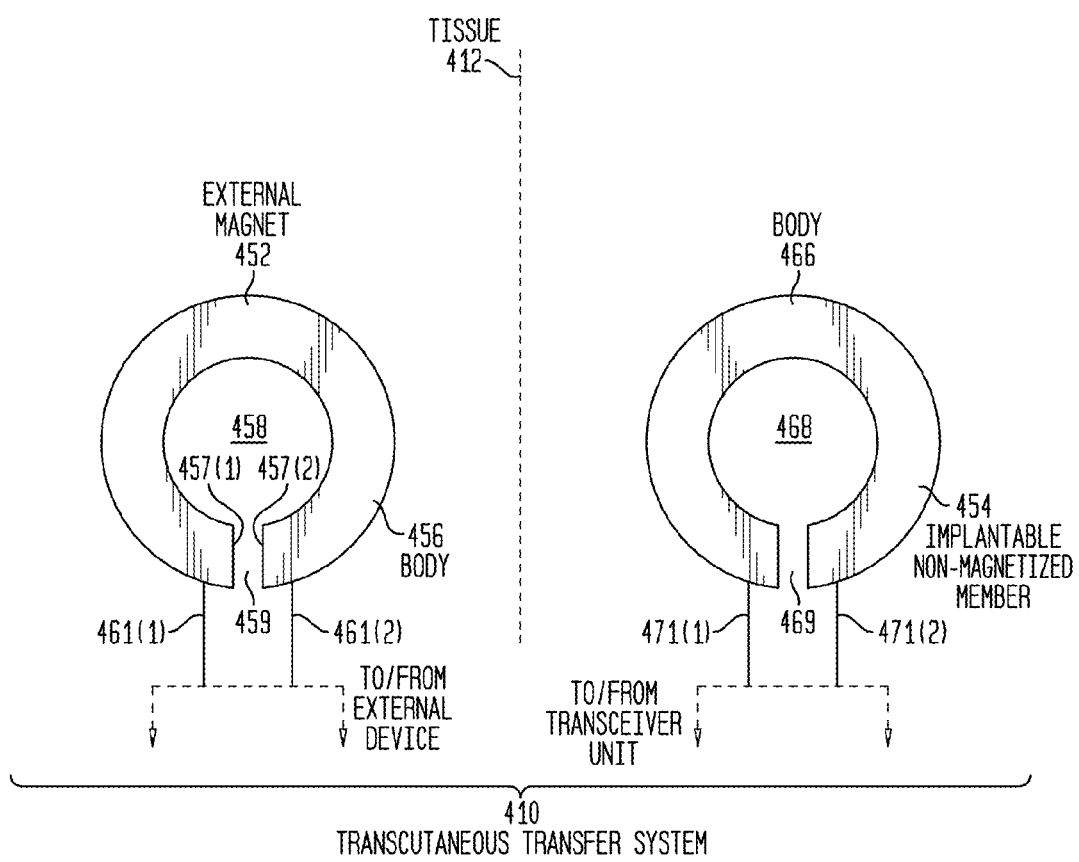

US 8,733,494 B1

COIL RETENTION SYSTEMS FOR IMPLANTABLE MEDICAL DEVICES

BACKGROUND

1. Field of the Invention

The present invention relates generally to implantable medical devices, and more particularly, to coil retention systems for implantable medical devices.

2. Related Art

Medical devices having one or more implantable components, generally referred to herein as implantable medical devices, have provided a wide range of therapeutic benefits to recipients over recent decades. In particular, partially or fully-implantable medical devices such as hearing prostheses (e.g., bone conduction devices, mechanical stimulators, cochlear implants, etc.), implantable pacemakers, defibrillators, functional electrical stimulation devices, and other implantable medical devices, have been successful in performing life saving and/or lifestyle enhancement functions for a number of years.

The types of implantable medical devices and the ranges of functions performed thereby have increased over the years. For example, many implantable medical devices now often include one or more instruments, apparatus, sensors, processors, controllers or other functional mechanical or electrical components that are permanently or temporarily implanted in a recipient. These functional components perform diagnosis, prevention, monitoring, treatment or management of a disease or injury or symptom thereof, or to investigate, replace or modify of the anatomy or of a physiological process. Many of these functional components utilize power and/or data received from external components that are part of, or operate in conjunction with, the implantable medical device.

SUMMARY

In one aspect of the invention, a transcutaneous system is provided. The transcutaneous system comprises an implantable non-magnetized member having a central aperture, and an external magnet having a central aperture configured to magnetically couple to the implantable non-magnetized member.

In another aspect of the present invention, a method is provided. The method comprises forming an implantable component of a transcutaneous transfer system comprising an implantable non-magnetized member having a central aperture and one or more conductive coils, and forming an external component of a transcutaneous transfer system comprises an external magnet having a central aperture configured to magnetically couple to the implantable non-magnetized member and one or more conductive coils.

BRIEF DESCRIPTION OF THE DRAWINGS

Embodiments of the present invention are described herein in conjunction with the accompanying drawings, in which:

FIG. 2A is a schematic side-view of a transcutaneous system comprising a coil retention system in accordance with embodiments of the present invention;

FIG. 3A is a schematic side-view of a transcutaneous system comprising a coil retention system in accordance with embodiments of the present invention;

FIG. 4A is a schematic side-view of a transcutaneous system comprising a coil retention system in accordance with embodiments of the present invention;

DETAILED DESCRIPTION

Embodiments are generally directed to coil retention systems for use in implantable medical devices. In certain embodiments, a coil retention system comprises an implantable non-magnetized member having a central aperture and an external magnet also having a central aperture. The external magnet is configured to magnetically couple to the implantable non-magnetized member. In certain embodiments, the external magnet and the implantable non-magnetized member have corresponding annular shapes so as to self-align with one another.

There are different types of implantable medical devices having a wide variety of corresponding implantable components that may be partially or fully implanted into a recipient. For example, implantable medical devices may include hearing prostheses (e.g., auditory brain stimulators, bone conduction devices, mechanical stimulators, cochlear implants, etc.), sensors, implantable pacemakers, defibrillators, functional electrical stimulation devices, catheters, etc. Many of these implantable medical devices utilize power and/or data received from external components that are part of, or operate in conjunction with, the implantable medical device. It is to be appreciated that coil retention systems in accordance with embodiments of the present invention may be used in connection with any of the above or other implantable medical devices. However, merely for ease of description, embodiments of the coil retention systems are primarily described herein in connection with one exemplary implantable medical device, namely a cochlear implant (also commonly referred to as cochlear implant device, cochlear prosthesis, and the like; simply "cochlear implant" herein).

Figure 1:
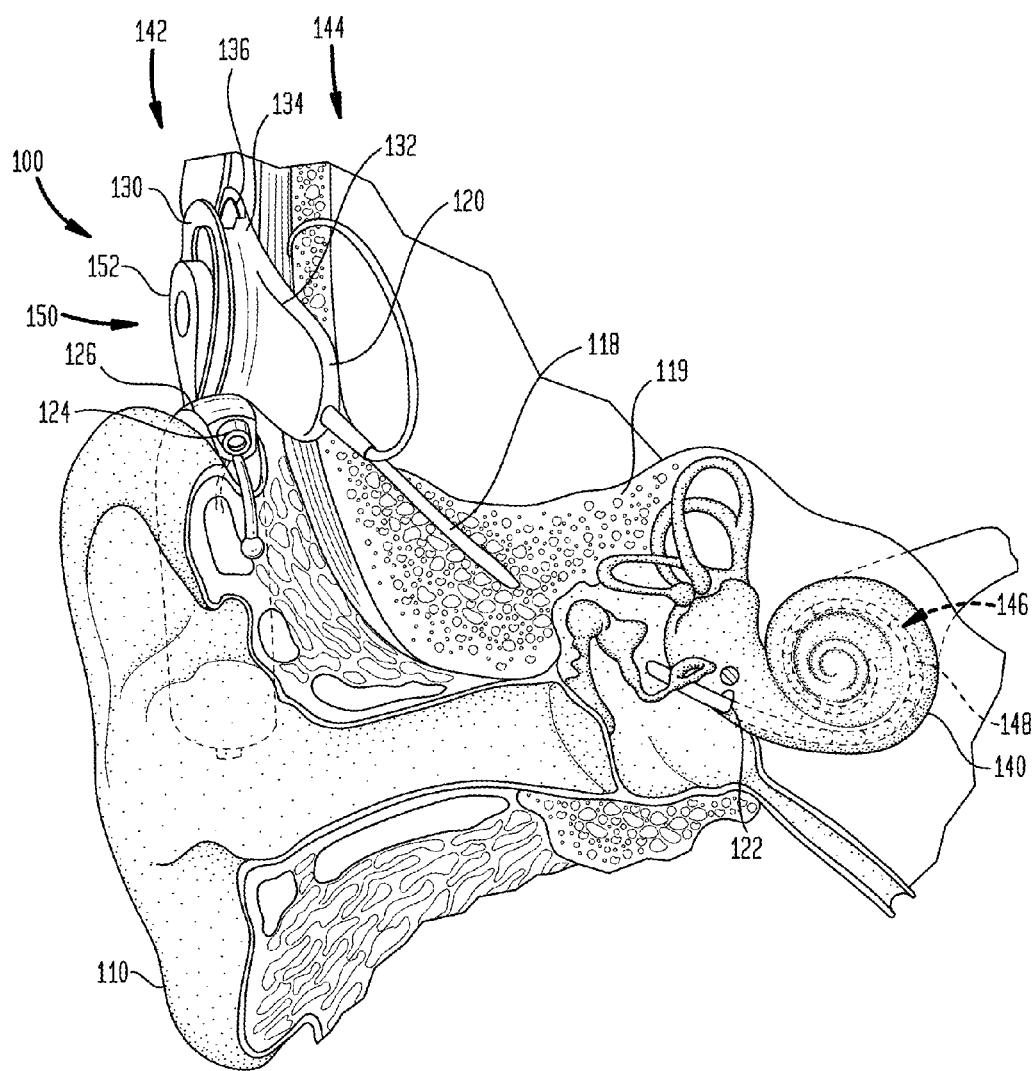
FIG. 1 is a schematic diagram of a cochlear implant having a coil retention system in accordance with embodiments of the present invention.

FIG. 1 is perspective view of an exemplary cochlear implant 100 comprising a coil retention system in accordance with embodiments of the present invention. In the example of FIG. 1, cochlear implant 100 comprises an external component 142 and an internal or implantable component 144. The external component 142 is directly or indirectly attached to the body of the recipient and typically comprises one or more sound input elements 124 (e.g., microphones, telecoils, etc.) for detecting sound, a sound processor 126, a power source (not shown), and an external coil 130. The sound processor 126 processes electrical signals generated by a sound input element 124 that is positioned, in the depicted embodiment, by auricle 110 of the recipient. The sound processor 126 provides the processed signals to external coil 130 via a cable (not shown).

The internal component 144 comprises an elongate stimulating assembly 118, a stimulator unit 120, and an internal receiver/transceiver unit 132, sometimes referred to herein as transceiver unit 132. Internal transceiver unit 132 and stimulator unit 120 are sometimes collectively referred to herein as a stimulator/transceiver unit and are coated/embedded in a flexible silicone molding 134. This silicone molding 134 is sometimes referred to as an overmold. In use, the stimulator/transceiver unit may be positioned in a recess of the temporal bone of the recipient.

Elongate stimulating assembly 118 has a proximal end connected to the stimulator unit 120 and a distal end implanted in cochlea 140. Elongate stimulating assembly 118 also includes a contact array 146 that comprises a plurality of stimulating contacts 148 that may be electrical and/or optical contacts. Stimulating assembly 118 extends from stimulator unit 120 to cochlea 140 through mastoid bone 119 and a cochleostomy 122.

The transceiver unit 132 is connected to an internal or implantable coil 136 that may also be embedded in the silicone molding 134. A part of silicone molding 134 has been omitted from FIG. 1 to expose a portion of the internal coil 136.

In the embodiments of FIG. 1, cochlear implant 100 comprises a coil retention system 150 that facilitates operational alignment of the external coil 130 and the internal coil 136 such that external and internal coils are inductively coupled to one another. That is, the coil retention system 150 is configured to retain the external coil 130 and the internal coil 136 in a position relative to one another such that the internal coil 136 may receive power and/or data from, and/or transmit power and/or data to, the external coil 130. In certain examples, external coil 130 transmits electrical signals (e.g., power and stimulation data) to internal coil 136 via a radio frequency (RF) link.

Coil retention system 150 comprises, in the example of FIG. 1, an external magnetized member 152 (external magnet) and an implantable non-magnetized member (not shown in FIG. 1). As described further below, the external magnetized member 152 and the implantable non-magnetized member may have corresponding generally annular shape so as to self-align with one another.

FIG. 2A is schematic side view of a transcutaneous transfer system 210 configured to transfer electrical signals (e.g., power and/or data) through the skin, muscle, fat, etc. (collectively referred to herein as tissue 212) of a recipient. In the example of FIG. 2A, transcutaneous transfer system 210 comprises an external coil 230, an internal or implantable coil 236, and a coil retention system 250. External coil 230 is configured to be positioned externally-adjacent to a recipient's tissue 212 (i.e., next to the recipient's skin) so as to inductively transfer electrical signals to, and/or inductively receive electrical signals from, internal coil 236 implanted in the recipient. External coil 230 and implantable coil 236 may each comprise multiple turns of electrically insulated single-strand or multi-strand wire. The wire may comprise, for example, platinum or gold. The ends of the external coil 230 are connected to an external device (e.g., sound processor), while the ends of the implantable coil 236 are connected to an implantable receiver or transceiver.

For efficient inductive transfer of signals between the external coil 230 and the internal coil 236, the coils should be substantially aligned with one another. That is, the external coil 230 should to be held on the outside of the recipient's body at a location such that the external coil and the implantable coil are substantially parallel to one another and arranged around the same central axis. In conventional transcutaneous systems, this alignment is achieved through the use of two cylindrical magnets, one disposed at the center of the external coil and one disposed at the center of the implantable coil. The poles of the cylindrical magnets are oriented so that they will be magnetically attracted to one another and it this mutual attraction that holds the external coil in alignment with the implantable coil.

These conventional transcutaneous systems, which require two magnets (one external and one implanted in the recipient), have several disadvantages. For example, magnetic fields generated during a Magnetic Resonance Imaging (MRI) scan can impart translation forces (torque) on an implanted magnet. Torque occurs because the poles of the implanted magnet try to align with the applied magnetic field. This torque can cause discomfort, pain, and/or damage to the device containing the magnet or to the surrounding tissue. Linear forces will also act on the implanted magnetic.

Additionally, the implanted magnet may generate artifacts during the MRI scan that affect the quality of the scan results. Furthermore, during an MRI scan, the implanted magnet may become demagnetized. Arrangements may use materials that resist demagnetization in low magnetic field strengths (e.g., certain materials experience only a 10% demagnetization within a field strength of 1.5 Tesla). However, the same materials may be significantly demagnetized at higher magnetic field strengths (e.g., 90% demagnetized within field strengths of 3 Tesla).

Embodiments of the present invention are generally directed to coil retention systems that may be used to align external and implantable coils without the need for an implanted magnet. More specifically, FIG. 2A illustrates an arrangement where the alignment between external coil 230 and the internal coil 236 is provided by coil retention system 250 that comprises an external member 252 and an internal or implantable member 254. The external member 252 is formed from a ferromagnetic or ferrimagnetic material and the external member 252 is magnetized. As such, external member 252 is sometimes referred to herein as an external magnetized member or simply external magnet 252.

The implantable member 254 is also formed from a ferromagnetic or ferrimagnetic material. However, unlike the external member 252, the implantable member 254 is not magnetized (i.e., non-magnetized). As such, implantable member 254 is sometimes referred to herein as implantable non-magnetized member 254. Although the implantable member 254 is non-magnetized, the implantable member is still formed from a material (e.g., a ferromagnetic or ferrimagnetic material) to which magnetized materials are magnetically attracted. For example, when the external magnet 252 is positioned in proximity to the implantable non-magnetized member 254, the external magnet 252 will be magnetically attracted to the implantable non-magnetized member 254.

In certain embodiments, the implantable non-magnetized member 254 may be formed from a ferromagnetic or ferrimagnetic material that is potentially toxic to a recipient. In such embodiments, the implantable non-magnetized member 254 is encased in a hermetically-sealed and biocompatible housing (not shown) that separates the potentially toxic material from the recipient's tissue and body fluid. In alternative embodiments, the implantable non-magnetized member 254 may be formed from a ferromagnetic or ferrimagnetic material that is biocompatible, thereby alleviating the need for a hermetic housing.

Figure 2B:
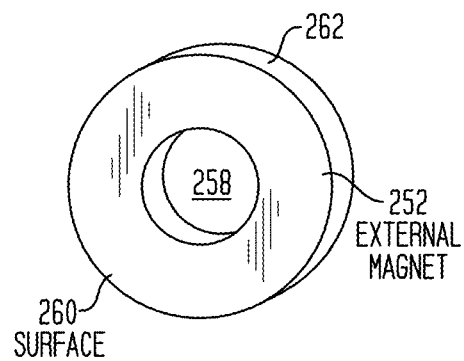
FIG. 2B is a perspective view of an external member of a coil retention system in accordance with embodiments of the present invention.

In the example of FIG. 2A, external magnet 252 has a generally annular shape. That is, external magnet 252 comprises an annular main body 256 disposed around a central aperture 258. External magnet 252 also has a surface 260 that is configured to be positioned adjacent to the recipient's tissue 212. The external coil 230 is disposed around the outer edge 262 of the external magnet 252 so as to be substantially co-axial with the external magnetized member 252. FIG. 2B is a perspective view of external magnet 252. For ease of illustration, the external coil 230 has been omitted from FIG. 2B.

Figure 2C:
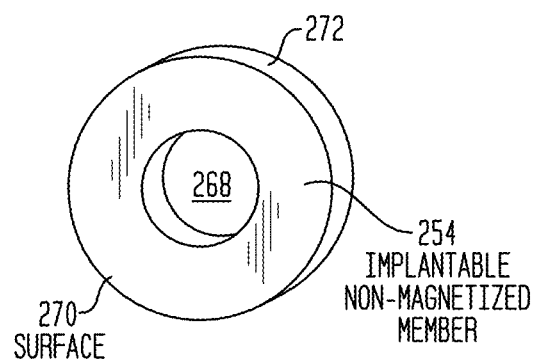
FIG. 2C is a perspective view of an implantable member of a coil retention system in accordance with embodiments of the present invention.

As shown in FIG. 2A, implantable non-magnetized member 254 also has a generally annular shape. That is, implantable non-magnetized member 254 comprises an annular main body 266 disposed around a central aperture 268. Implantable non-magnetized member 254 also has a surface 270 that is configured to, when implanted, face towards the recipient's tissue 212. The internal coil 236 is disposed around the outer edge 272 of the implantable non-magnetized member 254 so as to be substantially co-axial with the implantable non-magnetized member 254. FIG. 2C is a perspective view of implantable non-magnetized member 254. For ease of illustration, the internal coil 236 has been omitted from FIG. 2B.

In the embodiments of FIG. 2A, the external magnet 252 and the implantable non-magnetized member 254 have corresponding annular shapes. As used herein, corresponding annular shapes are annular shapes that facilitate self-alignment of the external magnet 252 and the implantable non-magnetized member 254. More specifically, in the example of FIG. 2A, the external magnet 252 and the implantable non-magnetized member 254 have corresponding annular shapes because the main bodies 256 and 266 are substantially the same size and the areas of surfaces 260 and 270 are substantially equal.

In alternative examples, the external magnet 252 and the implantable non-magnetized member 254 have corresponding annular shapes when one of the main bodies 256 or 266 has a larger size and surface area 260 or 270, respectively, than the other. However, in such examples, the external magnet 252 and the implantable non-magnetized member 254 may have substantially the same size central apertures.

In embodiments where external magnet 252 and the implantable non-magnetized member 254 have corresponding annular shapes, the magnetic attraction between the external magnet 252 and the implantable non-magnetized member 254 is strongest when the surfaces 260 and 272 are substantially aligned with one another. However, as a result of the corresponding annular shapes, the magnetic attraction forces will drop rapidly when the surfaces 260 and 272 are not aligned with one another (i.e., with misalignment). This drop off in magnetic attraction (facilitated by the shapes of the external magnet 252 and the implantable non-magnetized member 254) facilitates self-alignment of the external magnet 252 and the implantable non-magnetized member 254.

As noted above, the external coil 230 is disposed around the external magnet 252, while the implantable coil 236 is disposed around the implantable non-magnetized member 254. As such, because the external magnet 252 and the implantable non-magnetized member 254 are configured to align with one another via magnetic attraction, the external coil 230 and the implantable coil 236 will also be aligned with one another so as to facilitate transcutaneous transfer of electrical signals through the recipient's tissue 212. The magnetic attraction force between the external magnet 252 and the implantable non-magnetized member 254 is also such that, absent an external force to remove the external coil 230, the external coil 230 will remain in an aligned position with the implantable coil 236. By using a non-magnetized member as the implantable portion of the coil retention system 250, the coil retention system 250 does not suffer from the same drawbacks prevalent in conventional arrangements. In particular, because implantable member 254 is already non-magnetized, the implantable member cannot be demagnetized during an MRI scan and the implantable member will generate less significant artifacts during the scan. Additionally, no torque will be imparted to the non-magnetized element and linear forces will be significantly less than that imparted to an implanted magnetized member.

FIG. 3A is schematic side view of a transcutaneous transfer system 310 in accordance with embodiments of the present invention. In the example of FIG. 3A, transcutaneous transfer system 310 comprises an external coil 330, an internal or implantable coil 336, and a coil retention system 350. External coil 330 is configured to be positioned externally-adjacent to a recipient's tissue 312 so as to inductively transfer electrical signals to, and/or inductively receive electrical signals from, implantable coil 336 implanted in the recipient.

For efficient inductive transfer of signals between the external coil 330 and the internal coil 336, the coils should be substantially aligned with one another. In the example of FIG. 3A, the alignment between external coil 330 and the internal coil 336 is provided by coil retention system 350 that comprises an external member 352 and an internal or implantable member 354. The external member 352 is formed from a ferromagnetic or ferrimagnetic material that is magnetized. As such, external member 352 is sometimes referred to herein as an external magnetized member or simply external magnet 352.

The implantable member 354 is also formed from a ferromagnetic or ferrimagnetic material. However, unlike the external member 352, the implantable member 354 is not magnetized. As such, implantable member 354 is sometimes referred to herein as implantable non-magnetized member 354. Although the implantable member 354 is non-magnetized, the implantable member is still formed from a material (e.g., a ferromagnetic or ferrimagnetic material) to which magnetized materials are magnetically attracted. For example, when the external magnet 352 is positioned in proximity to the implantable non-magnetized member 354, the external magnet 352 will be magnetically attracted to the implantable non-magnetized member 354.

In certain embodiments, the implantable non-magnetized member 354 may be formed from a ferromagnetic or ferrimagnetic material that is potentially toxic to a recipient. In such embodiments, the implantable non-magnetized member 354 is encased in a hermetically-sealed and biocompatible housing (not shown) that separates the potentially toxic material from the recipient's tissue and body fluid. In alternative embodiments, the implantable non-magnetized member 354 may be formed from a ferromagnetic or ferrimagnetic material that is biocompatible, thereby alleviating the need for a hermetic housing.

External magnet 352 comprises an elongate body 356 having a first end 357(1) and a second end 357(2). The elongate body 356 is formed into a substantially annular shape so as to form a central aperture 358 and such that the first and seconds 357(1) and 357(2) are separated from one another by a gap 359. Elongate body 356 may have, for example, a circular, square, or rectangular cross-section.

Figure 3B:
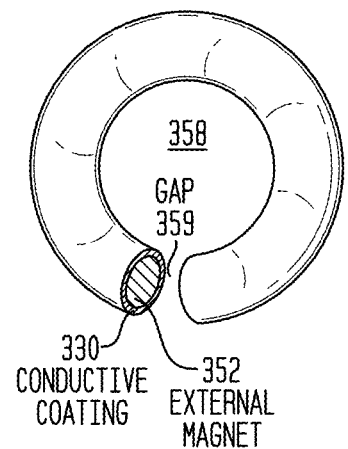
FIG. 3B is a perspective view of an external member of a coil retention system in accordance with embodiments of the present invention.

In the example of FIG. 3A, the external coil 330 is a conductive coating that is disposed on at least a portion of the outer surface of external magnet 352. A portion of the conductive coating 330 has been omitted from FIG. 3A to illustrate portions of the external magnet 352. FIG. 3B is a perspective view of external magnet 352 and conductive coating 330. The conductive coating 330 may comprise, for example, platinum or gold. The conductive coating 330 is connected to an external device via wires 361(1) and 361(2).

It is to be appreciated that the conductive coating 330 may be deposited on the surface of external magnet 352 in a number of different manners. In certain embodiments, the external magnet 352 and the conductive coating 330 comprise co-extruded members. That is, the external magnet 352 and the coating material may be fed through a single die so that the external magnet 352 and the coating material merge and weld together into a laminar structure. Alternatively, the coating may be replaced by a conductive layer fabricated in a separate operation. For example, the conductive layer could be formed from one or more pieces of sheet metal which are laser welded to form the outer layer.

As shown in FIG. 3A, implantable non-magnetized member 354 also comprises an elongate body 366 having a first end 367(1) and a second end 367(2). The elongate body 366 is formed into a substantially annular shape so as to form a central aperture 368 and such that the first and seconds 367(1) and 367(2) are separated from one another by a gap 369. Elongate body 366 may have, for example, a circular, square, or rectangular cross-section.

Figure 3C:
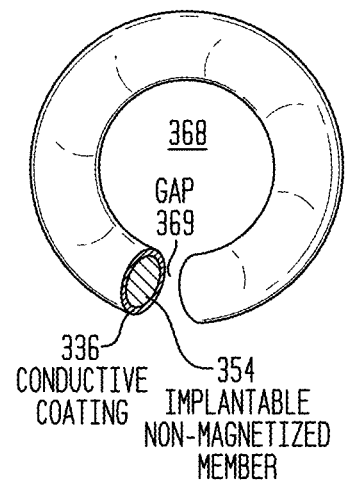
FIG. 3C is a perspective view of an implantable member of a coil retention system in accordance with embodiments of the present invention.

In the example of FIG. 3A, the implantable coil 336 is a conductive coating that is disposed on at least a portion of the outer surface of implantable non-magnetized member 354. A portion of the conductive coating 336 has been omitted from FIG. 3A to illustrate portions of the implantable non-magnetized member 354. FIG. 3C is a perspective view of implantable non-magnetized member 354 and conductive coating 336. The conductive coating 336 may comprise, for example, platinum or gold. The conductive coating 336 is connected to an external device via wires 371(1) and 371(2).

It is to be appreciated that the conductive coating 336 may be deposited on the surface of implantable non-magnetized member 354 in a number of different manners. In certain embodiments, the implantable non-magnetized member 354 and the conductive coating 336 comprise co-extruded members. That is, the implantable non-magnetized member 354 and the coating material may be fed through a single die so that the implantable non-magnetized member 354 and the coating material merge and weld together into a laminar structure. Alternatively, the coating may be replaced by a conductive layer fabricated in a separate operation. For example, the conductive layer could be formed from one or more pieces of sheet metal which are laser welded to form the outer layer.

In the embodiments of FIG. 3A, the external magnet 352 and the implantable non-magnetized member 354 have corresponding annular shapes that facilitate self-alignment of the external magnet 352 and the implantable non-magnetized member 354. More specifically, in the example of FIG. 3A, the external magnet 352 and the implantable non-magnetized member 354 have corresponding annular shapes because the main bodies 356 and 366 are substantially the same size. In alternative examples, the external magnet 352 and the implantable non-magnetized member 354 have corresponding annular shapes when one of the main bodies 356 or 366 has a larger size than the other. However, in such examples, the external magnet 352 and the implantable non-magnetized member 354 may have substantially the same size central apertures.

In embodiments where external magnet 352 and the implantable non-magnetized member 354 have corresponding annular shapes, the magnetic attraction between the external magnet 352 and the implantable non-magnetized member 354 is strongest when the annular shapes are substantially aligned with one another. However, the magnetic attraction forces will drop rapidly when the annular shapes are not aligned with one another (i.e., with misalignment). This drop off in magnetic attraction (facilitated by the shapes of the external magnet 352 and the implantable non-magnetized member 354) ensures self-alignment of the external magnet 352 and the implantable non-magnetized member 354.

As noted above, the external coil 330 is a conductive coating disposed on the surface of external magnet 352. Similarly, the implantable coil 336 is disposed on the surface of the implantable non-magnetized member 354. As such, because the external magnet 352 and the implantable non-magnetized member 354 are configured to align with one another via magnetic attraction, the external coil 330 and the implantable coil 336 will also be aligned with one another so as to facilitate transcutaneous transfer of electrical signals through the recipient's tissue 312. The magnetic attraction force between the external magnet 352 and the implantable non-magnetized member 354 is also such that, absent an external force to remove the external coil 330, the external coil 330 will remain in an aligned position with the implantable coil 336. By using a non-magnetized member as the implantable portion of the coil retention system 350, the coil retention system 350 does not suffer from the same drawbacks prevalent in conventional arrangements. In particular, because implantable member 354 is already non-magnetized, the implantable member cannot be demagnetized during an MRI scan and the implantable member will generate less significant artifacts during the scan. Additionally, no torque will be imparted to the non-magnetized element and linear forces will be significantly less than that imparted to an implanted magnetized member.

FIGS. 3A-3C illustrate embodiments of the present invention in which a conductive coating is disposed on substantially the entire surface of an external magnet or an implantable non-magnetized member. This configuration has several advantage. For example, if the non-magnetic material is potential toxic and the conductor is biocompatible, the conductor can provide the dual role of conductive coil and biocompatible barrier. Additionally, the electric field lines from the conductor (used as an RF coil) do not pass through the conductive material of the non-magnetized unit and hence eddy current losses are reduced.

Figure 3D:
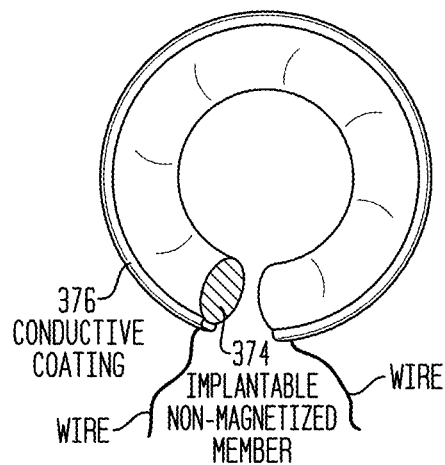
FIG. 3D is a perspective view of an implantable member of a coil retention system in accordance with embodiments of the present invention.

It is to be appreciated that the embodiments of FIGS. 3A-3C are merely illustrative and that the conductive coatings may have different arrangements in alternative embodiments of the present invention. For example, FIG. 3D illustrates one alternative embodiment of the present invention in which a conductive coating 376 is disposed on the surface of an implantable non-magnetized member 374. In contrast to the embodiments of FIGS. 3A-3C, in the embodiments of FIG. 3D the conductive coating 376 is disposed in a linear strip on the outer edge of the implantable non-magnetized member 374. That is, a majority of the surface of implantable non-magnetized member 374 is not covered by the conductive coating 376. In this embodiment, the linear strip of conductive coating 376 operates as an implantable coil that may be inductively coupled to one or more external coils.

Figure 3E:
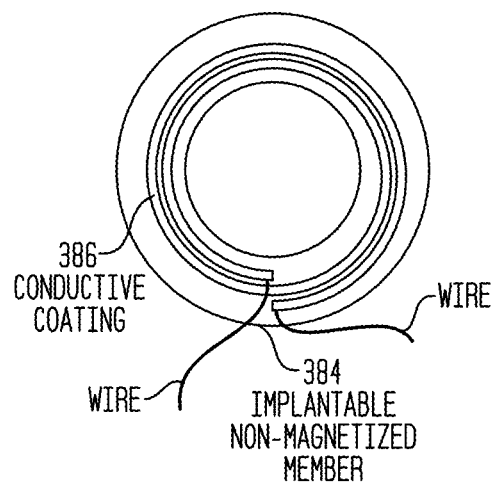
FIG. 3E is a perspective view of an implantable member of a coil retention system in accordance with embodiments of the present invention.

FIG. 3E illustrates another embodiment of the present invention in which a conductive coating 386 is disposed on the surface of an implantable non-magnetized member 384. In contrast to the embodiments of FIGS. 3A-3C, in the embodiments of FIG. 3E the implantable non-magnetized member 384 forms a complete toroid (i.e., no gap). Additionally, the conductive coating 386 is disposed in a circuitous pattern forming, in this example, two loops of the coating on the surface of the implantable non-magnetized member 384. A majority of the surface of the implantable non-magnetized member 384 is not covered by the conductive coating 386. In this embodiment, the two loops of the conductive coating 386 operate as an implantable coil that may be inductively coupled to one or more external coils.

FIG. 4A is schematic side view of a transcutaneous transfer system 410 in accordance with embodiments of the present invention. In the example of FIG. 4A, transcutaneous transfer system 410 comprises an external member 452 and an internal or implantable member 454. The external member 452 is formed from a ferromagnetic or ferrimagnetic material and is magnetized. As such, external member 452 is sometimes referred to herein as an external magnetized member or simply external magnet 452.

External magnet 452 comprises an elongate body 456 having a first end 457(1) and a second end 457(2). The elongate body 456 is formed into a substantially annular shape so as to form a central aperture 458 and such that the first and seconds 457(1) and 457(2) are separated from one another by a gap 459. Elongate body 456 may have, for example, a circular, square, or rectangular cross-section.

The implantable member 454 is also formed from a ferromagnetic or ferrimagnetic material. However, unlike the external member 452, the implantable member 454 is not magnetized. As such, implantable member 454 is sometimes referred to herein as implantable non-magnetized member 454. Although the implantable member 354 is non-magnetized, the implantable member is still formed from a material (e.g., a ferromagnetic or ferrimagnetic material) to which magnetized materials are magnetically attracted. For example, when the external magnet 452 is positioned in proximity to the implantable non-magnetized member 454, the external magnet 452 will be magnetically attracted to the implantable non-magnetized member 454.

As shown in FIG. 4A, implantable non-magnetized member 454 also comprises an elongate body 466 having a first end 467(1) and a second end 467(2). The elongate body 466 is formed into a substantially annular shape so as to form a central aperture 468 and such that the first and second ends 467(1) and 467(2) are separated from one another by a gap 469. Elongate body 466 may have, for example, a circular, square, or rectangular cross-section.

Figure 4B:
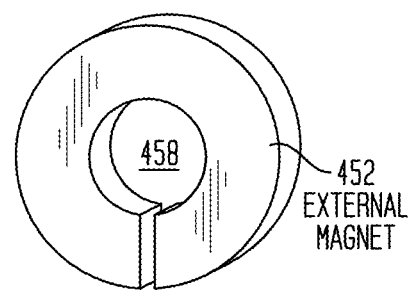
FIG. 4B is a perspective view of an external member of a coil retention system in accordance with embodiments of the present invention.
Figure 4C:
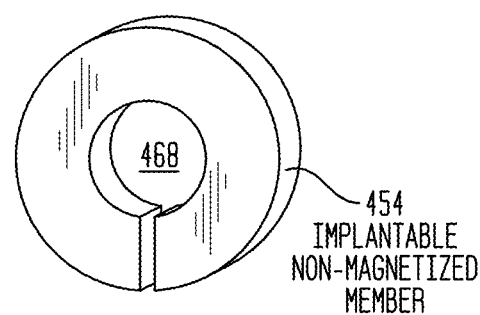
FIG. 4C is a perspective view of an implantable member of a coil retention system in accordance with embodiments of the present invention.

In the example of FIG. 4A, the external magnet 452 and the implantable non-magnetized member 454 are each formed a conductive material such that external magnet and the implantable non-magnetized member may operate as transfer coils for the transcutaneous transfer system 410. More specifically, first end 457(1) is connected to an external device via a wire 461(1), while second end 457(1) is also connected to the external device via a wire 461(2). Similarly, first end 467(1) of implantable non-magnetized member 454 is connected to a receiver/transceiver unit via wire 471(1), while second end 467(1) is also connected to the receiver/transceiver unit via a wire 471(2). In one embodiment, the wires 461(1) or 461(2) are used to pass current through the external magnet so as to generate a magnetic field that is detected by the implantable non-magnetized member 454. Because the implantable non-magnetized member 454 is also conductive, the magnetic field generated by the external magnet 452 will also induce current to flow in the implantable non-magnetized member 454. As such, in the example of FIG. 4A, external magnet 452 and implantable non-magnetized member 454 are inductively coupled so as to transcutaneous transfer signals through the recipient's tissue 412. FIG. 4B is a perspective view of external magnet 452. FIG. 4C is a perspective view of implantable non-magnetized member 354.

In the embodiments of FIGS. 4A-4C, the external magnet 452 and the implantable non-magnetized member 454 have corresponding annular shapes that facilitate self-alignment with one another. More specifically, in the example of FIG. 4A, the external magnet 452 and the implantable non-magnetized member 454 have corresponding annular shapes because the main bodies 456 and 466 are substantially the same size.

In alternative examples, the external magnet 452 and the implantable non-magnetized member 454 have corresponding annular shapes when one of the main bodies 456 or 466 has a larger size than the other. However, in such examples, the external magnet 452 and the implantable non-magnetized member 454 may have substantially the same size central apertures.

In embodiments where external magnet 452 and the implantable non-magnetized member 454 have corresponding annular shapes, the magnetic attraction between the external magnet 452 and the implantable non-magnetized member 454 is strongest when the annular shapes are substantially aligned with one another. However, the magnetic attraction forces will drop rapidly when the annular shapes are not aligned with one another (i.e., with misalignment). This drop off in magnetic attraction (facilitated by the shapes of the external magnet 452 and the implantable non-magnetized member 454) ensures self-alignment of the external magnet 452 and the implantable non-magnetized member 454.

As noted above, the external magnet 452 operates as an external coil to transcutaneously transfer electrical signals to implantable non-magnetized member 454 operating as an implantable coil. The magnetic alignment between the external magnet 452 and the implantable non-magnetized member 454 facilitates efficient transcutaneous transfer of electrical signals through the recipient's tissue 412. The magnetic attraction force between the external magnet 452 and the implantable non-magnetized member 454 is also such that, absent an external force to remove the external magnet 452, the external magnet will remain in an aligned position with the implantable non-magnetized member 454. By using a non-magnetized member as the implantable portion of the transcutaneous transfer system 410, the system does not suffer from the same drawbacks prevalent in conventional arrangements. In particular, because implantable member 454 is already non-magnetized, the implantable member cannot be demagnetized during an MRI scan and the implantable member will not generate artifacts during the scan. Additionally, no torque will be imparted to the non-magnetized element and linear forces will be significantly less than that imparted to an implanted magnetized member.

In embodiments of FIGS. 4A-4C, the implantable non-magnetized member 454 is formed from a non-toxic material that may be implanted in a recipient without any type of casing/barrier that separates the implantable non-magnetized member 454 from the recipient's tissue and body fluids. In certain such embodiments, the implantable non-magnetized member 454 is formed from a cobalt platinum alloy. Certain cobalt platinum alloys have good magnetic properties, may be drawn into desired shapes/sizes (e.g., wires), are conductive, and are inert for biocompatibility. In alternative embodiments, the implantable non-magnetized member 454 may be formed from a material that is potentially toxic to a recipient. In such embodiments, the implantable non-magnetized member 454 is encased in a hermetically-sealed and biocompatible housing (not shown) that separates the potentially toxic material from the recipient's tissue and body fluid.

FIGS. 2A-2C, 3A-3C, and 4A-4C illustrate different arrangements for external or internal components of a transcutaneous transfer system in accordance with embodiments of the present invention. However, it is to be appreciated that the embodiments of FIGS. 2A-2C, 3A-3C, and 4A-4C are not mutually exclusive and that the various embodiments may be combined with one another in a number of different manners.

Figure 5:
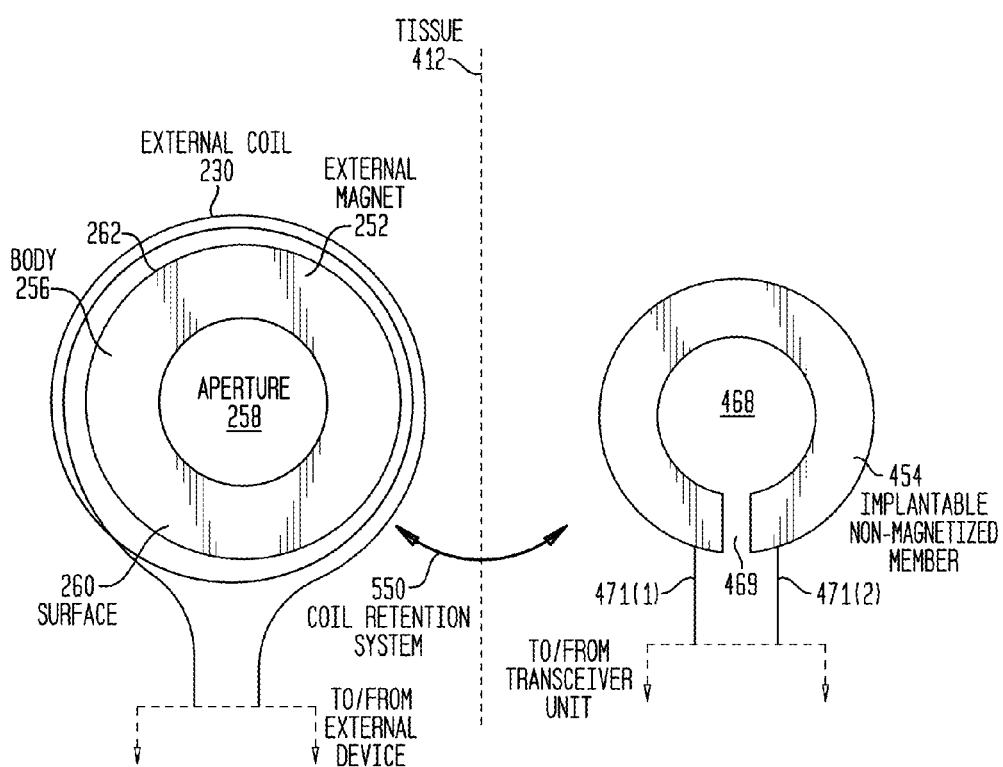
FIG. 5 is a schematic side-view of a transcutaneous system comprising a coil retention system in accordance with embodiments of the present invention.

For example, FIG. 5 illustrates an embodiment where the external magnet 252 and external coil 230 of FIG. 2A are used with the implantable non-magnetized member 454 of FIG. 4A. In these embodiments, the external magnet 252 and the implantable non-magnetized member 454 collectively form a coil retention system 550.

Figure 6:
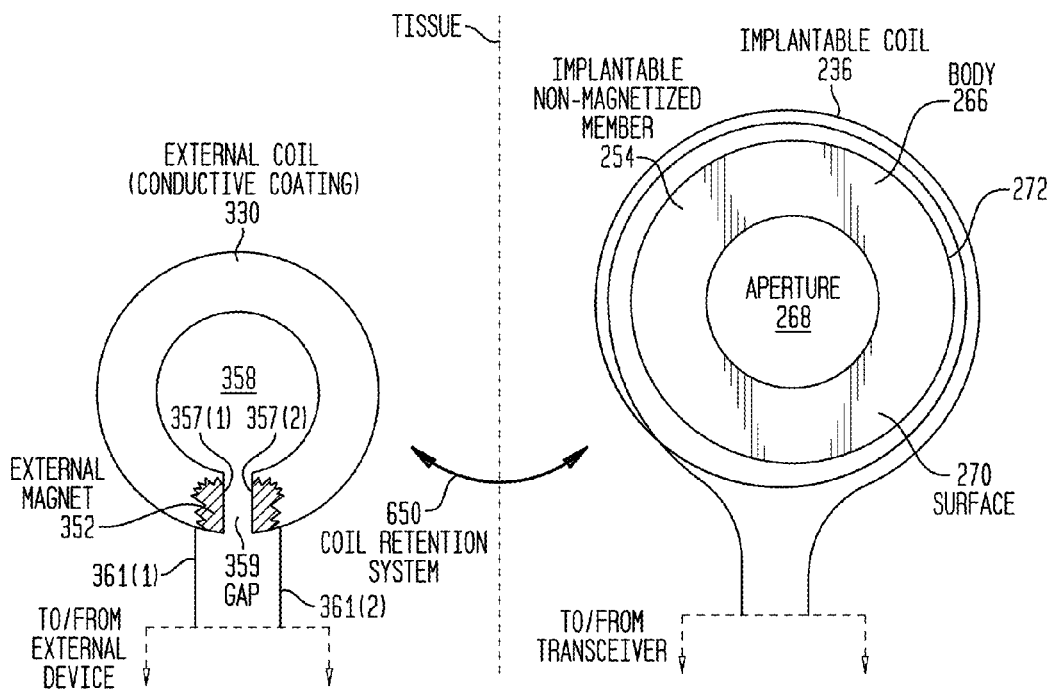
FIG. 6 is a schematic side-view of a transcutaneous system comprising a coil retention system in accordance with embodiments of the present invention.

FIG. 6 illustrates another embodiment where the external magnet 352 and external coil 330 of FIG. 3A are used with the implantable non-magnetized member 254 and implantable coil 236 of FIG. 2A. In these embodiments, the external magnet 352 and the implantable non-magnetized member 254 collectively form a coil retention system 650.

Figure 7:
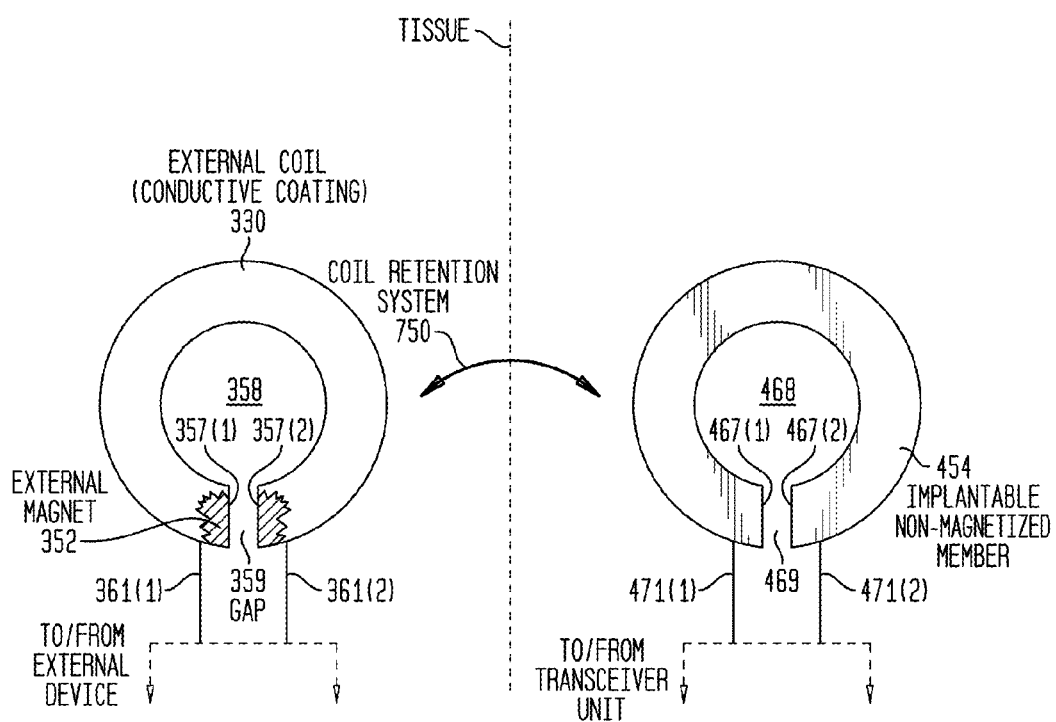
FIG. 7 is a schematic side-view of a transcutaneous system comprising a coil retention system in accordance with embodiments of the present invention.

FIG. 7 illustrates a further embodiment where the external magnet 352 and external coil 330 of FIG. 3A are used with the implantable non-magnetized member 454 of FIG. 4A. In these embodiments, the external magnet 352 and the implantable non-magnetized member 454 collectively form a coil retention system 750.

FIGS. 2A to 7 illustrate embodiments of the present invention where the external magnets and the implantable non-magnetized members having substantially annular shapes. In particular, the annular shapes shown in FIGS. 2A to 7 are substantially toroid shapes. It is to be appreciated that other shapes for external magnets and the implantable non-magnetized members may be used in alternative embodiments of the present invention. For example, in such alternative embodiments, external magnets and implantable non-magnetized members may have oval, square, rectangular, or other shapes.

Figure 8A:
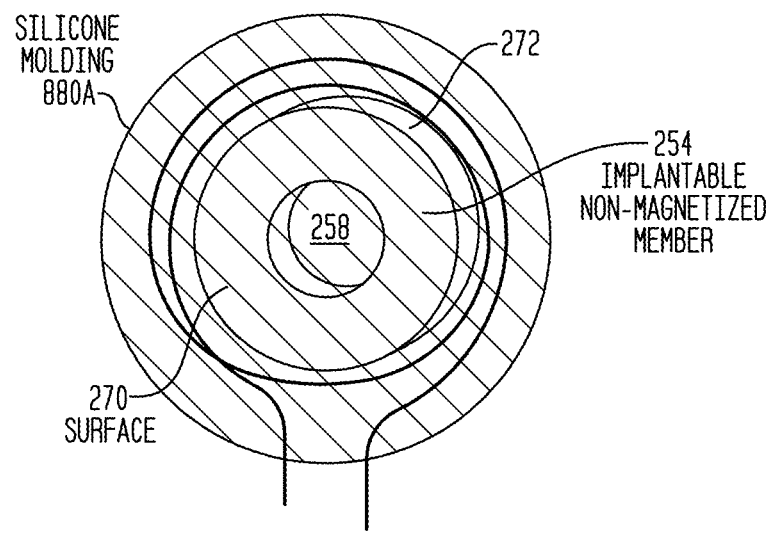
FIG. 8A is a perspective view of an implantable member of a coil retention system disposed in a silicone mold in accordance with embodiments of the present invention.

In certain embodiments, an implantable non-magnetized member and/or internal coil are both disposed in a biocompatible molding. The molding may be, for example, formed from silicone. FIG. 8A illustrates an embodiment where the implantable non-magnetized member 254 and implantable coil 236 are disposed in a silicone molding 880A. In this example, the silicone molding 880A fills the aperture 268 at the center of the implantable non-magnetized member 254. In the embodiments of FIG. 8A, the silicone filled aperture 268 stiffens the structure so that the implantable non-magnetized member 254 is more robust to forces, such as forces generated during an MRI scan.

Figure 8B:
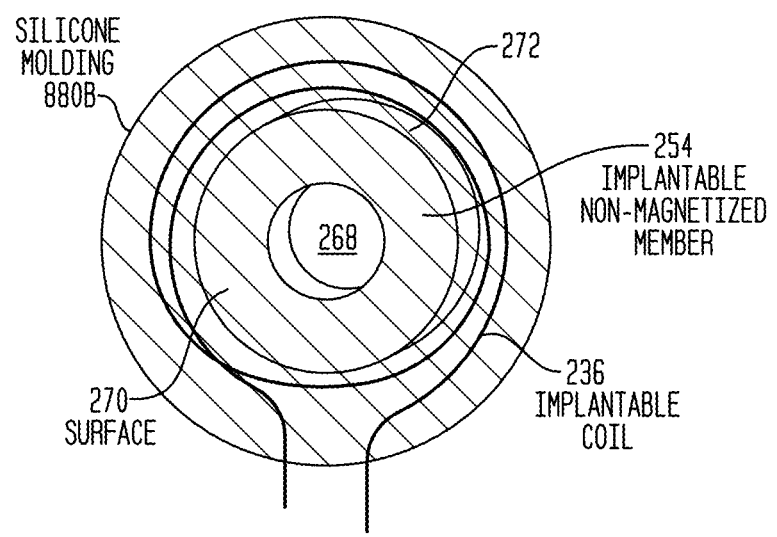
FIG. 8B is a perspective view of an implantable member of a coil retention system disposed in a silicone mold in accordance with embodiments of the present invention.

FIG. 8B illustrates an alternative embodiment where the implantable non-magnetized member 254 and implantable coil 236 are disposed in a silicone molding 880B. In this example, the silicone molding 880B entirely covers the surface of the implantable non-magnetized member 254, but aperture 268 at the center of the implantable non-magnetized member 254 remains substantially unobstructed. That is, the silicone molding 880B does not fill the aperture 268. In the embodiments of FIG. 8B, because the aperture 268 remains unobstructed, tissue is free to grow through the aperture following implantation into a recipient. In this case, the tissue that grows through the aperture 268 functions as a constraining mechanism to make the implantable non-magnetized member 254 more robust to forces, such as forces generated during an MRI scan or an external impact.

As noted above, implantable non-magnetized member in accordance with embodiments of the present invention may be formed from a biocompatible material that is safe for direct implantation into a recipient. Alternatively, the implantable non-magnetized member may be formed from a potentially toxic material and, as such, is encased in a hermetically sealed housing that operates as a barrier between the potentially toxic material and the recipient's tissue and body fluid. In certain embodiments of the present invention, the implantable non-magnetized member, or a hermetic housing in which the implantable non-magnetized member is positioned, may include one or more surface features that are configured to facilitate attachment of the implantable non-magnetized member (or housing) to the recipient's tissue.

Figure 9A:
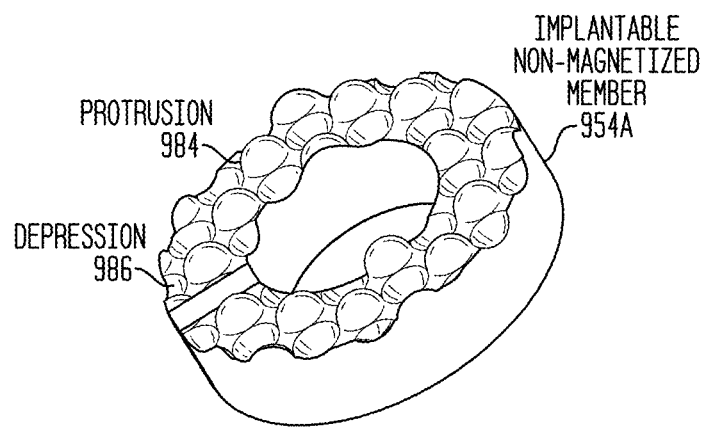
FIG. 9A is a perspective view of an implantable member of a coil retention system having surface features disposed thereon in accordance with embodiments of the present invention.

For example, FIG. 9A is perspective view of an implantable non-magnetized member 954A configured to be directly implanted into a recipient. In this embodiment, implantable non-magnetized member 954A is formed from a biocompatible and conductive material having magnetic properties (e.g., a cobalt platinum alloy). Implantable non-magnetized member 954A includes surface features in the form of depressions 986 defined by spaced protrusions 984. The protrusions 984 have a generally parabolic or dome shape and are disposed across a surface of implantable non-magnetized member 954A that is configured to be positioned adjacent to a recipient's tissue. In operation, the recipient's tissue and/or bone may, over time, grow into the depressions 986 so as to secure implantable non-magnetized member 954A within the recipient.

FIG. 9A illustrates embodiments with protrusions 984 having a generally parabolic shape. It is to be appreciated that alternative embodiments may use different shapes (i.e., square, rectangular, arcuate, etc.) for protrusions 984. Also, the depressions 986 may be formed through the creation of protrusions 984 or vice versa. It is also to be appreciated that other embodiments may include only depressions 986 or only protrusions 984.

Figure 9B:
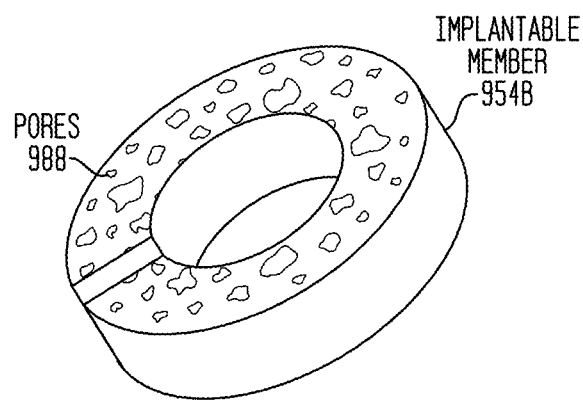
FIG. 9B is a perspective view of an implantable member of a coil retention system having surface features disposed thereon in accordance with embodiments of the present invention.

FIG. 9B is perspective view of another implantable non-magnetized member 954B configured to be directly implanted into a recipient (i.e., the implantable non-magnetized member 954A is formed from a biocompatible and conductive material having magnetic properties). Implantable non-magnetized member 954B includes surface features in the form of pores 988 that are disposed across a surface of implantable non-magnetized member 954B that is configured to be positioned adjacent to a recipient's tissue. In operation, the recipient's tissue and/or bone may, over time, grow into the pores 988 so as to secure implantable non-magnetized member 954B within the recipient. In certain embodiments, the pores 988 may be chemically etched into the surface of the implantable non-magnetized member 954B.

Figure 10:
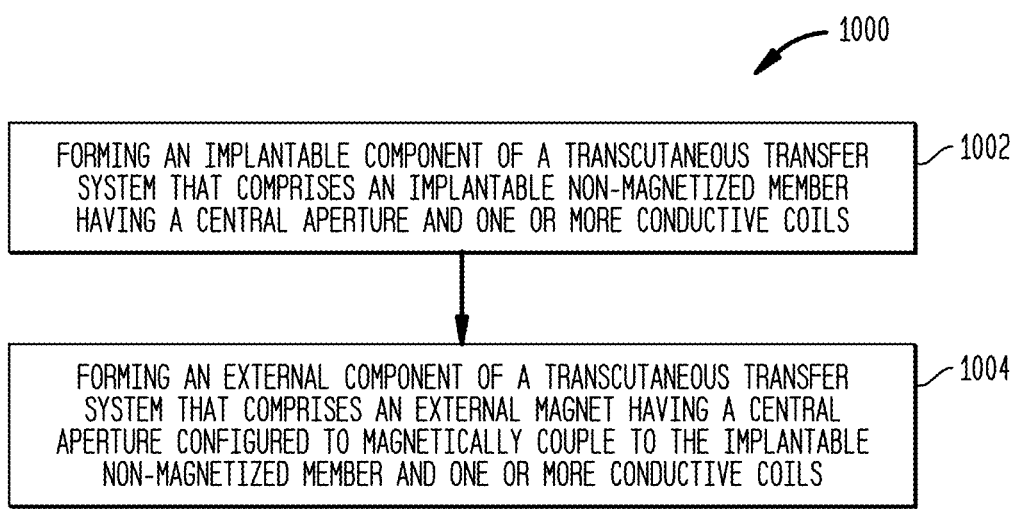
FIG. 10 is a flowchart of a method in accordance with embodiments of the present invention.

FIG. 10 is a flowchart of a method 1000 for manufacturing a transcutaneous system in accordance with embodiments of the present invention. Method 100 begins at 1002 where an implantable component of a transcutaneous transfer system is formed. In the embodiments of FIG. 10, the implantable component comprises an implantable non-magnetized member having a central aperture and one or more conductive coils. At 1004, an external component of a transcutaneous transfer system is formed. In the embodiments of FIG. 10, the external component comprises an external magnet having a central aperture configured to magnetically couple to the implantable non-magnetized member and one or more conductive coils.

In certain embodiments, the implantable component of the transcutaneous transfer system may be formed by obtaining a toroid implantable non-magnetized member having a central aperture and positioning or more conductive coils around the implantable non-magnetized member. Similarly, the external component of the transcutaneous transfer system may also be formed by obtaining a toroid external magnet having a central aperture, and positioning one or more conductive coils around the external magnet.

In other embodiments, the implantable component of the transcutaneous transfer system may be formed by forming a non-magnetized elongate member into a substantially toroid shape, and depositing a conductive coating on a surface of the non-magnetized elongate member. The conductive coating operates as the one or more conductive coils of the implantable component. Similarly, the external component of the transcutaneous transfer system may be formed by forming an elongate magnet into a substantially toroid shape, and depositing a conductive coating on a surface of the elongate magnet. The conductive coating operates as the one or more conductive coils of the external component.

In further embodiments, the implantable component of the transcutaneous transfer system may be formed by forming a demagnetized elongate member into a substantially toroid shape. In such embodiments, the demagnetized elongate member is formed from a conductive material such that the demagnetized elongate member operates as the one or conductive coils of the implantable component. Similarly, the external component of the transcutaneous transfer system may be formed by forming an elongate magnet into a substantially toroid shape. The external magnet is formed from a conductive material such that the external magnet operates as the one or conductive coils of the external component.

As noted above, embodiments of the present invention are generally directed to coil retention systems comprising an implantable non-magnetized member having a central aperture and an external magnet also having a central aperture. In these embodiments, force generated on the implantable non-magnetized member during, for example, an MRI scan are spread over a larger area (relative to conventional cylindrical magnets), thereby reducing the risk of discomfort and damage to the device or surrounding tissue. The use of non-magnetized material (instead of a magnet) in the implant also reduces the risks associated with MRI scans. Additionally, the use of corresponding annular shapes facilities self-alignment and the annular shape of an external magnet allow greater freedom in design that may result in better comfort and aesthetics. The annular shape of an implantable member also allows greater freedom in design that may result in better magnet retention.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A transcutaneous system comprising:
   a substantially toroid shaped implantable ferromagnetic or ferrimagnetic non-magnetized member having a central aperture;
   one or more implantable coils associated with the implantable non-magnetized member;
   one or more external coils; and
   a substantially toroid shaped external magnet associated with the one or more external coils, wherein the external magnet has a central aperture and is configured to magnetically couple to the implantable non-magnetized member so as to align the one or more external coils with the one or more implantable coils.

2. The transcutaneous system of claim 1, wherein the external magnet and the implantable non-magnetized member each comprises first and second substantially planar parallel surfaces, and wherein the first and second surfaces of the external magnet have substantially the same surface area as the first and second surfaces of the implantable non-magnetized member.

3. The transcutaneous system of claim 1, wherein the external magnet and the implantable non-magnetized member each comprises first and second substantially planar parallel surfaces, and wherein the first and second surfaces of the external magnet have a larger same surface area than the first and second surfaces of the implantable non-magnetized member.

4. The transcutaneous system of claim 1, wherein the external magnet comprises an elongate magnet formed into the substantially toroid shape, and wherein a conductive coating is disposed on an outer surface of the elongate magnet to form the one or more external coils.

5. The transcutaneous system of claim 1, wherein the implantable non-magnetized member comprises an elongate member formed into the substantially toroid shape, and wherein a conductive coating is disposed on an outer surface of the elongate member that operates as the one or more implantable coils.

6. The transcutaneous system of claim 1, wherein the external magnet comprises an elongate magnet formed into the substantially toroid shape, and wherein the external magnet is formed from a conductive material so as to operate as the one or more external coils for inductive coupling with the one or more implantable coils.

7. The transcutaneous system of claim 1, wherein the implantable non-magnetized member comprises an elongate member formed into the substantially toroid shape, and wherein the implantable non-magnetized member is formed from a conductive material so as to operate as the one or more implantable coils for inductive coupling with the one or more external coils.

8. The transcutaneous system of claim 7, wherein the implantable non-magnetized member is formed from a cobalt-platinum alloy.

9. The transcutaneous system of claim 7, wherein the implantable non-magnetized member includes one or more surface features configured to secure the implantable non-magnetized member to bone or tissue.

10. The transcutaneous system of claim 1, wherein the implantable non-magnetized member is encased in silicone molding such that the molding substantially fills the central aperture of the implantable non-magnetized member.

11. The transcutaneous system of claim 1, wherein the implantable non-magnetized member is encased in a silicone molding such that the central aperture of the implantable non-magnetized member is substantially unobstructed.

12. A method comprising:
    forming an implantable component of a transcutaneous transfer system comprising one or more implantable coils and a substantially toroid shaped implantable ferromagnetic or ferrimagnetic non-magnetized member having a central aperture; and
    forming an external component of a transcutaneous transfer system comprising one or more external coils and a substantially toroid shaped external magnet having a central aperture configured to magnetically couple to the implantable non-magnetized member so as to align the one or more external coils with the one or more implantable coils.

13. The method of claim 12, wherein forming the implantable component of the transcutaneous transfer system comprises:
    obtaining the toroid shaped implantable non-magnetized member; and
    positioning one or more wire conductors around the implantable non-magnetized member to form the one or more implantable coils.

14. The method of claim 12, wherein forming the external component of the transcutaneous transfer system comprises:
    obtaining the toroid shaped external magnet; and
    positioning one or more wire conductors around the external magnet.

15. The method of claim 12, wherein forming the implantable component of the transcutaneous transfer system comprises:
    forming a non-magnetized elongate member into a substantially toroid shape; and
    depositing a conductive coating on a surface of the non-magnetized elongate member, wherein the conductive coating operates as the one or more implantable coils of the implantable component.

16. The method of claim 12, wherein forming the external component of the transcutaneous transfer system comprises:
    forming an elongate magnet into a substantially toroid shape; and
    depositing a conductive coating on a surface of the elongate magnet, wherein the conductive coating operates as the one or more external coils of the external component.

17. The method of claim 12, wherein forming the implantable component of the transcutaneous transfer system comprises:
    forming an elongate member into a substantially toroid shape, wherein the elongate member is formed from a conductive material that also operates as the one or more implantable coils of the implantable component.

18. The method of claim 12, wherein forming the external component of the transcutaneous transfer system comprises:
    forming an elongate magnet into a substantially toroid shape, wherein the external magnet is formed from a conductive material that also operates as the one or more external coils of the external component.

19. An external component of a hearing prosthesis, comprising:
    a sound processor;
    one or more external coils electrically connected to the sound processor; and
    a substantially toroid shaped external magnet co-located with the one or more external coils configured to magnetically couple to an implantable toroid shaped ferromagnetic or ferromagnetic non-magnetized member so as to align the one or more external coils with one or more implantable coils co-located with the non-magnetized member.

20. The external component of claim 19, wherein the external magnet comprises an elongate magnet formed into the substantially toroid shape, and wherein a conductive coating is disposed on an outer surface of the elongate magnet to form the one or more external coils.

* * * * *